(12) United States Patent
Shen et al.

(10) Patent No.: US 11,097,139 B1
(45) Date of Patent: Aug. 24, 2021

(54) PROCESS FOR INHIBITING CORROSION IN DRY PIPE SPRINKLER SYSTEMS

(71) Applicant: Cortec Corporation, White Bear Lake, MN (US)

(72) Inventors: Mincheng Shen, Eagan, MN (US); Sen Kang, Oakdale, MN (US); Boris A. Miksic, Longboat Key, FL (US)

(73) Assignee: Cortec Corporation, White Bear Lake, MN (US)

(*) Notice: Subject to any disclaimer, the term of this patent is extended or adjusted under 35 U.S.C. 154(b) by 94 days.

(21) Appl. No.: 15/985,062

(22) Filed: May 21, 2018

Related U.S. Application Data

(60) Provisional application No. 62/508,635, filed on May 19, 2017.

(51) Int. Cl.
*G01N 17/00* (2006.01)
*A62C 35/64* (2006.01)
*A62C 35/62* (2006.01)
*G01M 3/28* (2006.01)
*A62C 35/68* (2006.01)

(52) U.S. Cl.
CPC ............ *A62C 35/645* (2013.01); *A62C 35/62* (2013.01); *A62C 35/68* (2013.01); *G01M 3/2807* (2013.01); *G01N 17/00* (2013.01)

(58) Field of Classification Search
USPC .............................................. 73/86
See application file for complete search history.

(56) References Cited

U.S. PATENT DOCUMENTS

| | | | | |
|---|---|---|---|---|
| 2010/0263882 | A1* | 10/2010 | Bodemann | A62C 35/62 169/17 |
| 2014/0205496 | A1* | 7/2014 | Kharshan | C23F 11/02 422/9 |
| 2014/0332240 | A1* | 11/2014 | Kochelek | A62C 35/68 169/17 |
| 2016/0206907 | A1* | 7/2016 | O'Leary | A62C 35/68 |

FOREIGN PATENT DOCUMENTS

KR 20140027655 * 3/2014 ............. A62C 35/68

* cited by examiner

*Primary Examiner* — Daniel S Larkin
(74) *Attorney, Agent, or Firm* — Taft Stettinius & Hollister LLP; Daniel A. Rosenberg

(57) ABSTRACT

A corrosion prevention process to protect the piping of a dry pipe sprinkler system from corrosion is described. The process includes the selection and application of suitable corrosion inhibitors to interior portions of the piping. The corrosion inhibitors used in this process may include volatile corrosion inhibitors.

26 Claims, 7 Drawing Sheets

PROCESS FOR INHIBITING CORROSION IN DRY PIPE SPRINKLER SYSTEMS

RELATED APPLICATIONS

This application claims the benefit of priority of U.S. Provisional Patent Application No. 62/508,635, filed on May 19, 2017, which is incorporated by reference herein in its entirety.

BACKGROUND OF THE INVENTION

Sprinkler systems are commonly used to protect life and property from fire within buildings. Water is the most common agent used in such systems to extinguish fire or reduce its spread and severity. The basic elements of such a system include temperature activated sprinkler heads, a source of water, and a network of distribution pipes to transport the water to each sprinkler head. Water based sprinkler systems are further divided into wet pipe and dry pipe systems. In a wet pipe system, the distribution pipes are constantly pressurized with water. When a sprinkler head is activated, spraying of water begins effectively immediately. In a dry pipe system, the distribution pipes are typically pressurized with air or another gas. These pipes are connected to a remote water source. A check valve keeps the water from entering the distribution pipes until a triggering event. Dry pipe systems are typically more expensive to set up and maintain compared to a wet pipe system. Therefore, they are generally only used in specific situations, where a wet pipe system is not practical. This would include situations in which the distribution pipes would potentially freeze or in situations where a leak from a wet pipe system would have serious negative consequences.

After use or testing of a dry pipe system, the water is drained from the distribution pipes and the check valve is reset. In doing so, some amount of residual water remains in the distribution pipes, particularly at low points. This residual water, in the presence of air in the distribution pipes, can create highly corrosive conditions, leading to rusting of pipes which can ultimately lead to leaking (formation of holes) or plugging of the pipes (by rust debris). This is one of the major maintenance issues with a dry pipe system. Previously, the use of corrosion inhibitors (combined with antimicrobial agents) has been described for use in preventing corrosion in piping systems (including sprinkler systems such as the system described in U.S. Pat. No. 6,841,125, Chartier). This combination was prepared as an aqueous solution which was caused to foam (by sparging air into the liquid). Said foam was then directed through the piping to distribute the active agents. While potentially effective, such an approach is potentially quite messy and has never been widely adopted commercially for dry pipe systems. A more common approach is to purge the pipe with dry nitrogen, which gradually removes residual water and reduces the available oxygen. Such an approach is described in US20100263882A1 Bodemann, and US20160008644A1 Kochelek. While effective in reducing corrosion, such systems can be expensive to install and maintain. Thus, there remains a need for simple and cost effective systems to inhibit corrosion in dry pipe sprinkler systems.

Accordingly, the present invention concerns structures, systems, materials and processes directed to one or more of the following objects:

(1) to facilitate corrosion protection of dry pipe sprinkler systems;

(2) to provide a process for treating interior portions of water piping in dry pipe sprinkler systems; and (3) to provide compositions particularly well suited for protecting piping utilized in dry pipe sprinkler systems.

SUMMARY OF THE INVENTION

To achieve these and other objects, there is provided a corrosion protection system and process. The process includes selection and application of one or more suitable corrosion inhibitors to reduce or prevent corrosion of interior portions of piping in dry pipe sprinkler systems. The corrosion inhibitor, or corrosion inhibiting agent, may be a volatile corrosion inhibitor. In some embodiments, the corrosion inhibitor, or corrosion inhibiting agent, comprises at least two different volatile corrosion inhibitors.

In some embodiments, corrosion inhibitor is applied to the pipe interior as an aerosol product, which may be a suspension of solid particles or liquid droplets in a carrier gas.

In some embodiments, the aerosol may be a liquid aerosol comprising corrosion inhibitor dissolved or suspended in a solvent or carrier fluid.

In some embodiments, the aerosol may be a liquid aerosol comprising corrosion inhibitor which is liquid at the application temperature and which may be applied without need of a solvent or carrier liquid.

In some embodiments, the corrosion inhibitor may be a volatile material which is introduced in vapor form into the pipe.

In some embodiments, the corrosion inhibitor may be a volatile material which is introduced in vapor form into a carrier gas for application and distribution within the pipe.

In some embodiments, the volatile corrosion inhibitor or the carrier gas may be heated to increase the concentration of corrosion inhibitor in the vapor phase, for introduction into the pipe.

In some embodiments, the dry pipe system is stored pressurized with gas containing volatile corrosion inhibitors.

In some embodiments, a chamber or housing is provided in the piping system to allow a source of volatile corrosion inhibitor to contact gas that is used to pressurize the dry pipe system.

In some embodiments, a device to monitor corrosion is inserted into the piping, which may comprise test coupons or corrosion sensors.

In some embodiments, the process may comprise the sequential application of the corrosion inhibitor to different segments of the system.

In some embodiments, one or more additional entry/exit ports are added to a dry pipe sprinkler system to facilitate application of corrosion inhibitor. As used herein, the term "exit port" refers to any opening in the system including, but not limited to, drains, access ports, and sprinkler heads.

In some embodiments, a device to facilitate transport of the corrosion inhibitor from the source of the corrosion inhibitor to other locations in the dry pipe sprinkler system is included. The device to facilitate transport of the corrosion inhibitor may comprise a fan, a blower, a compressor, a pump, or a combination thereof.

In some embodiments, a vacuum or sub-ambient pressure is applied to an exit port of the dry pipe system to facilitate application of the corrosion inhibitor or distribution throughout the pipe system.

In some embodiments, a mechanical fan may be used to introduce vapor into an entrance port or draw vapor out of an exit port as a means to apply corrosion inhibitor to the piping.

In some embodiments, the vapor may be monitored at an exit port or a monitoring port to determine if a desired quantity of corrosion inhibitor is present in the piping.

In some embodiments, the application process may consist of two or more embodiments used sequentially. An example would be the use of an aerosol application method to provide immediate protection to a system about to be put back in service, followed by the use of a volatile corrosion inhibitor in the pressurized gas to assure long term protection while the system is in service.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Further features and advantages will become apparent upon consideration of the following detailed description and drawings, in which:

FIGS. 5-7 illustrate the steps that could be used to sequentially apply volatile corrosion inhibitor (VCI) to different portions of the piping system, with FIG. 5 illustrating the step of filling a first portion of the system with VCI, FIG. 6 illustrating the step of filling a second portion of the system with VCI, and FIG. 7 illustrating the long-term preservation of VCI in the system after it has been filled with VCI.

DETAILED DESCRIPTION OF THE PREFERRED EMBODIMENTS

Figure 1:
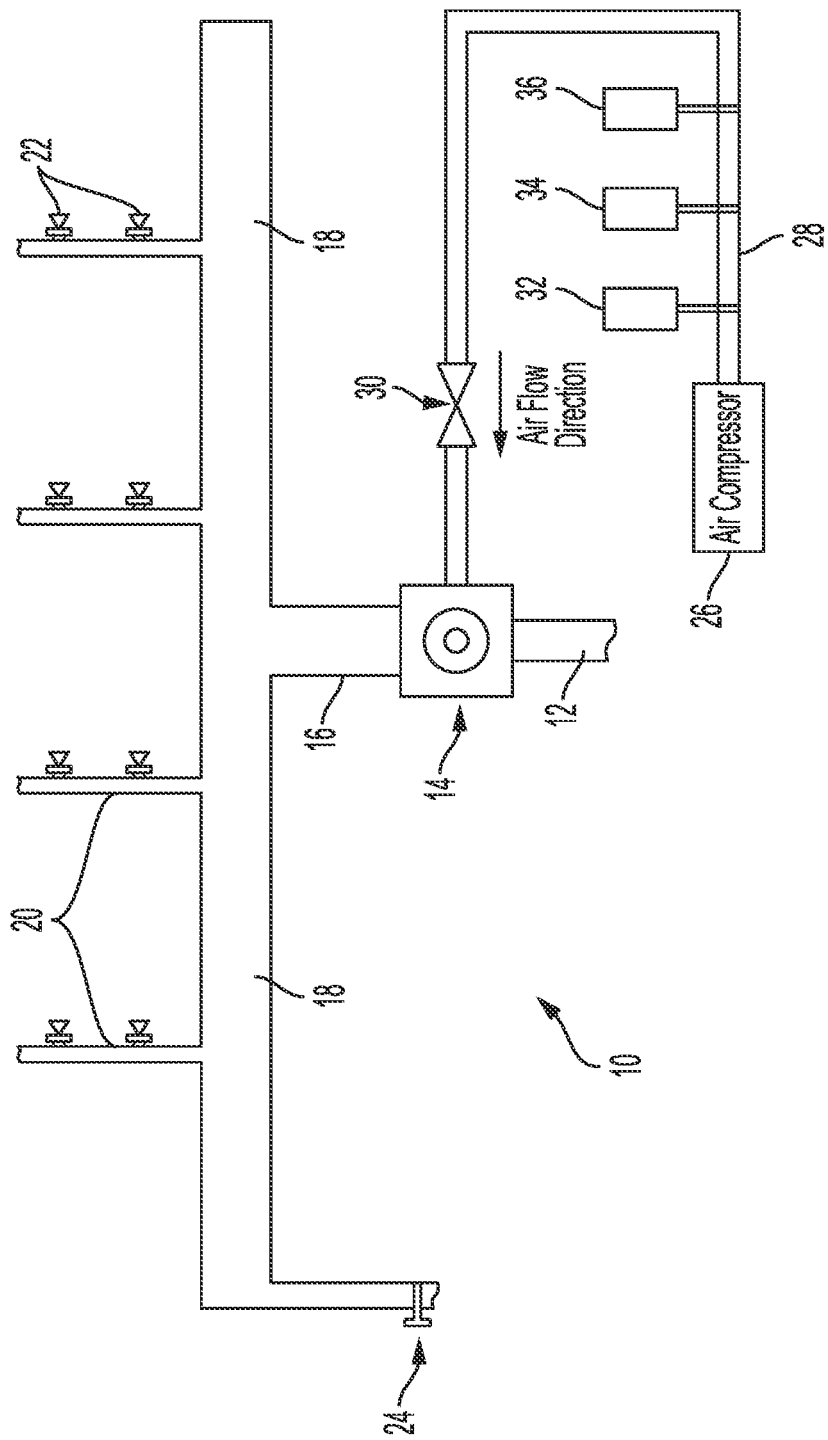
FIG. 1 is a schematic drawing showing the typical elements of a dry pipe sprinkler system.

Volatile corrosion inhibitors (VCI) are utilized in a variety of applications for protecting metal from corrosion. These are generally composed of chemicals which function as corrosion inhibitors and which are primarily in the solid or liquid state at ambient temperatures, but which exhibit a small but significant vapor pressure. This volatility enables the corrosion inhibitors to migrate in the vapor phase to effectively protect all metal surfaces in proximity (U.S. Pat. Nos. 2,752,221, 4,275,835). The volatile feature of the chemicals facilitates protection of exposed metal surfaces not accessible by other forms of corrosion inhibiting agents, especially deep recesses and voids within the interior volume. The VCI in the vapor stream adsorbs on the exposed metal surfaces, forming a thin, protective layer that provides continuous protection against corrosion from exposure to moisture, salt, oxygen, carbon dioxide, or other corrosive elements. If the layer is disturbed by moisture or other corrosive components entering the interior volume, the corrosion inhibiting characteristics remain effective if VCI remains in the system, such that the layer may be replenished with VCI.

One prevalent application of VCI involves protecting metal in an enclosed space, such as electronics in a closed classis or a metal article in a sealed package. In those situations, a vapor permeable packet containing a small amount of VCI can be inserted in the enclosure to provide corrosion protection to all contents for an extended period of time (up to several years). However, experience has shown that there are limits to the above approach. In non-closed systems, the VCI can be lost to the outside atmosphere. Even in closed systems, the extent of corrosion protection tends to diminish at distances more than several feet from the VCI material packet. This is particularly problematic in enclosures with a high aspect ratio (e.g. inside a pipe). For this reason, a number of alternate delivery vehicles have been developed to extend the use of VCI to a wider variety of applications (U.S. Pat. Nos. 3,084,022, 5,715,945, 5,332, 525, 6,028,160, 6,555,600, 9,435,037).

Non-limiting examples of volatile corrosion inhibitors which have been found highly effective for use in connection with the present invention are amine salts of nitrates, amine salts of nitrites, amine and ammonium salts of organic acids, amine carboxylates, alkali and amine dibasic acid salts, alkali nitrites, alkali nitrates, alkali molybdates, tall oil imidazolines, volatile amines, volatile organic acids, and triazole compounds. Other specific examples of corrosion inhibitor ingredients useful in this invention are described in the patents: U.S. Pat. Nos. 4,275,835, 5,715,975, 5,855,975, 6,028,160, 6,054,512, 6,085,905, 6,156,929, 6,555,600, 7,118,615, 7,264,707, and 7,763,213.

Non-limiting examples of preferred volatile corrosion inhibiting agents are selected from the group consisting of ammonium benzoate, cyclohexylammonium benzoate, monoethanolamine benzoate, dicyclohexyl ammonium nitrate, tolyltriazole, benzotriazole, their combinations, and other combinations of corrosion inhibitors such as the amine salts of acids such as sebacic acid and caprylic acid.

By passing a carrier gas through an enclosed space containing VCI, a vapor stream is created containing some quantity of VCI vapor. This vapor stream can then be used to distribute VCI throughout the interior volume. The carrier gas would typically be air, but other non-corrosive gases will also work. The carrier gas may preferably be depleted in corrosive compounds, such as water, saline aerosols, acids, sulfur compounds, etc. relative to ambient air.

In preferred embodiments, the VCI agent is supplied in a solid form. It can be conveniently supplied as a granular or powdered product. If the VCI agent is supplied in a solid form, it must be adapted so that it will not leave a residue that will interfere with water flow, prevent water from flowing from the sprinklers, or block or clog any components of the dry pipe sprinkler system. The VCI may also be provided in liquid form, or as a composition impregnated in a substrate. The substrate may include a foam, a pad, a gauze, or any other material which may be impregnated with a VCI agent. If the VCI agent, or substrate impregnated with VCI agent, is placed directly in a housing unit, the housing unit may include a barrier to limit the rate at which VCI agent is transmitted from the housing unit. Alternatively, the VCI agent, or substrate impregnated with VCI agent, may be enclosed in a vapor permeable pouch or package. The carrier gas is passed through the space surrounding the VCI agent, such that VCI vapor distributes in the carrier gas to become the effective vapor stream. The movement of the vapor stream through the interior volume of the structure provides corrosion protection to that interior volume.

Another aspect of the present invention is a process for treating interior surfaces of piping in a dry pipe sprinkler system. The dry pipe sprinkler system may be a fire suppression sprinkler system. The process includes the following steps:

a. generating a vapor stream including a dry carrier gas, and a volatile corrosion inhibiting agent with an affinity for metal surfaces; and b. introducing the vapor stream into the interior of the piping, until the vapor stream substantially fills an interior volume.

The vapor stream is introduced to the interior volume through an entrance passage, preferably near a first end region of pipe system. Simultaneously, the internal volume is evacuated by allowing flow through an exit passage, preferably at an opposite end region of the pipe system. For long piping systems, multiple entrances and exits over the length of the piping may be used with this process.

Flow of the vapor stream through the piping may be facilitated by positive pressure applied to the entrance or suction applied to the exit or both.

Another aspect of the present invention is a process for treating interior surfaces of piping in a dry pipe sprinkler system. The process includes the following steps:

a. forming an entrance passage;

b. forming an exit passage, spaced apart from the entrance passage;

c. generating an vapor stream including a carrier gas, and volatile corrosion inhibitor dispersed in the carrier gas;

d. introducing the vapor stream into the interior volume through the entrance passage while simultaneously allowing a flow out of the interior volume through the exit passage, to substantially fill the interior volume with the vapor stream; and e. with the interior volume substantially filled with the vapor stream, closing the entrance passage and the exit passage to maintain the VCI agent inside.

In accordance with the invention, the vapor stream may be provided into the interior volume through the entrance passage at low pressure, for example using a conventional air hose at a pressure of less than 100 psi. The vapor stream advances through the interior volume due to the continued positive pressure, while gases previously present in the interior volume flow out of the interior volume through the exit passage.

To achieve a faster treatment of the pipe with corrosion inhibitor or to load a larger quantity of corrosion inhibitor in the pipe, the corrosion inhibitor may be applied as an aerosol. Further, the aerosol may consist of solid or liquid material. The term "fogging" refers to the application of the corrosion inhibitor as a solid or liquid aerosol; especially when the particle or droplet sizes are large enough to be observed visually (as a fog or haze) in the carrier gas. The term "fogger" refers to a mechanical device which can suspend liquids or solid particles in a carrier gas to form an aerosol. A liquid sprayer may be suitable for use a liquid fogger, depending on the size of droplets that are produced.

If applied as a solid aerosol, it is advantageous that the inhibitor materials are supplied as powders and are dry; and preferably screened to an average particle size of about 0.2 mm or less. The screened particles may be subjected to a further size-reduction stage, such that the resulting powder is made up of particles with diameters less than about 50 microns.

If applied as a liquid aerosol, a liquid VCI material may be used, or a solution of VCI in a suitable solvent. Particle size of the liquid droplets can be controlled through selection of spray equipment and operating parameters.

Turning now to the drawings, FIG. 1 is a schematic drawing of a typical dry pipe sprinkler system 10. The sprinkler system 10 includes a water pipe 12 connected to a water supply. When a triggering event occurs, check valve 14 permits water to pass from water pipe 12 through connecting pipe 16 to main pipe 18 and distribution pipes 20. Water is then discharged from the distribution pipes 20 through the sprinkler heads 22. Water may be drained from the connecting pipe 16, main pipe 18, and distribution pipes 20 through the system drain 24. After use of the system 10, water is drained through the system drain 24 and check valve 14 is reset.

When the connecting pipe 16, main pipe 18, and distribution pipes 20 are not filled with water, they are typically pressurized with air. Air enters the system 10 from air compressor 26 and passes through air pipe 28, through an air regulator 30 and check valve 14, and through connecting pipe 16, main pipe 18, and distribution pipes 20. The air flow direction through the air regulator 30 is from air compressor 26 to check valve 14. Air pipe 28 may be connected to filter 32 so that air will be filtered prior to passing through air regulator 30. Dehumidifier 34 and desiccant 36 may be connected to air pipe 28 to reduce the moisture in the air before the air passes through air regulator 30.

The water in water pipe 12 may be at a pressure of 50 psi or less. The air pressure between air regulator 30 and check valve 14, and in connecting pipe 16, main pipe 18, and distribution pipes 20, may be 35 psi or less.

Figure 2:
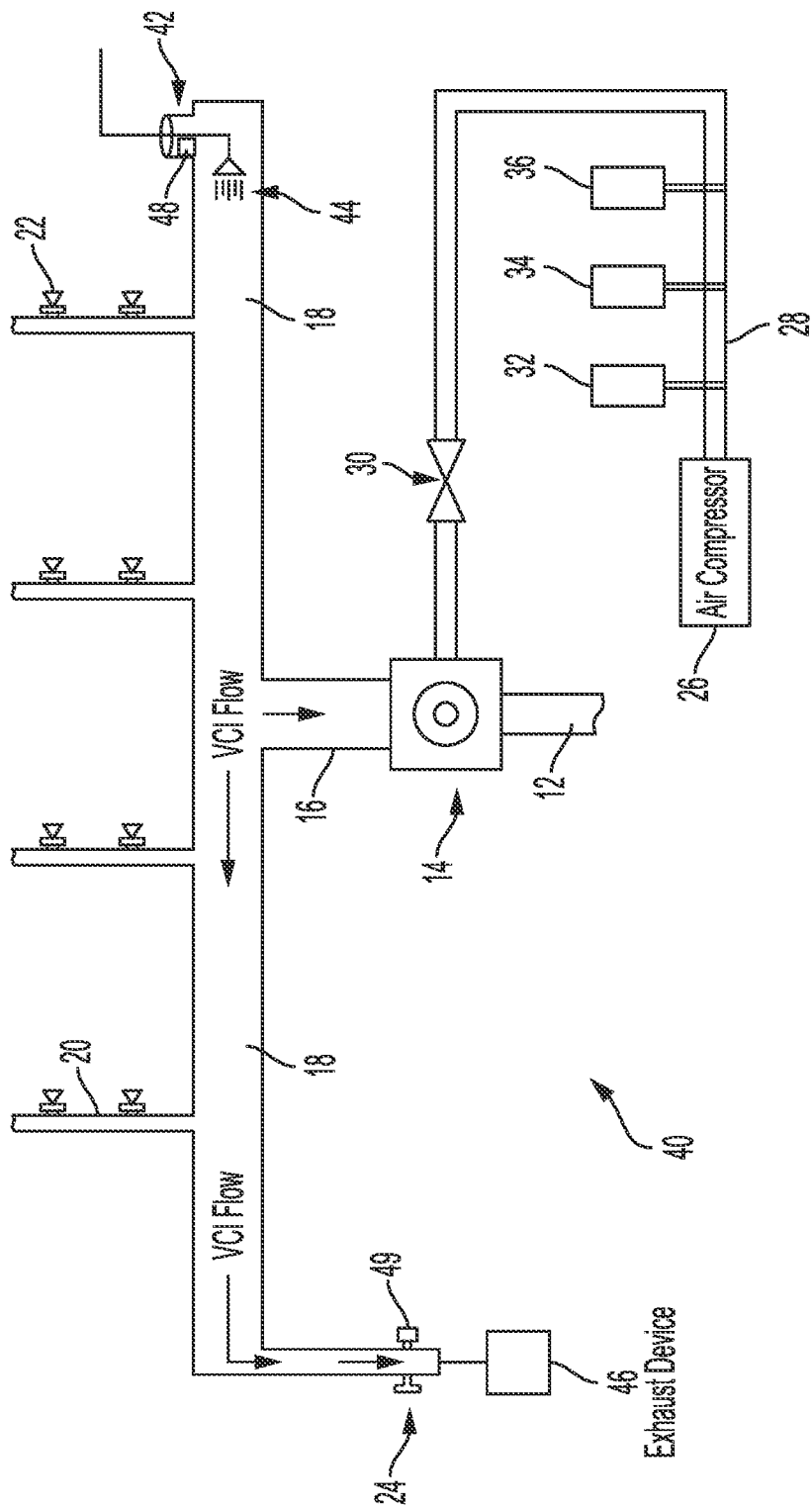
FIG. 2 is a schematic drawing of an embodiment of a dry pipe sprinkler system in accordance with the present invention, including modifications to support introduction of a volatile corrosion inhibitor at an inlet port.

FIG. 2 is a schematic drawing of sprinkler system 40, which is an embodiment of a dry pipe sprinkler system of the present invention. The sprinkler system 40 differs from typical sprinkler system 10 shown in FIG. 1 in that sprinkler system 40 includes an opening 42 in main pipe 18 to allow VCI to be fogged through pipes 16, 18, and 20. After air compressor 26 is shut off, the VCI enters the system through inlet 44. The VCI flows through main pipe 18, connecting pipe 16, and distribution pipes 20, and arrives at the system drain 24 with the aid of exhaust device 46. The exhaust device 46 may be a vacuum pump or a fan. The usage of exhaust device 46 is optional. A corrosion monitoring device 48, such as a weighing coupon or corrosion sensor, may be inserted through opening 42 and held within pipe 18 to monitor corrosion rate. A monitoring device or VCI detection device 49 may be placed at the system drain 24 to monitor the level of VCI. The corrosion monitoring device 48 may be located at various locations in system 40. Moreover, a plurality of corrosion monitoring devices 48 may be located in system 40.

Figure 3:
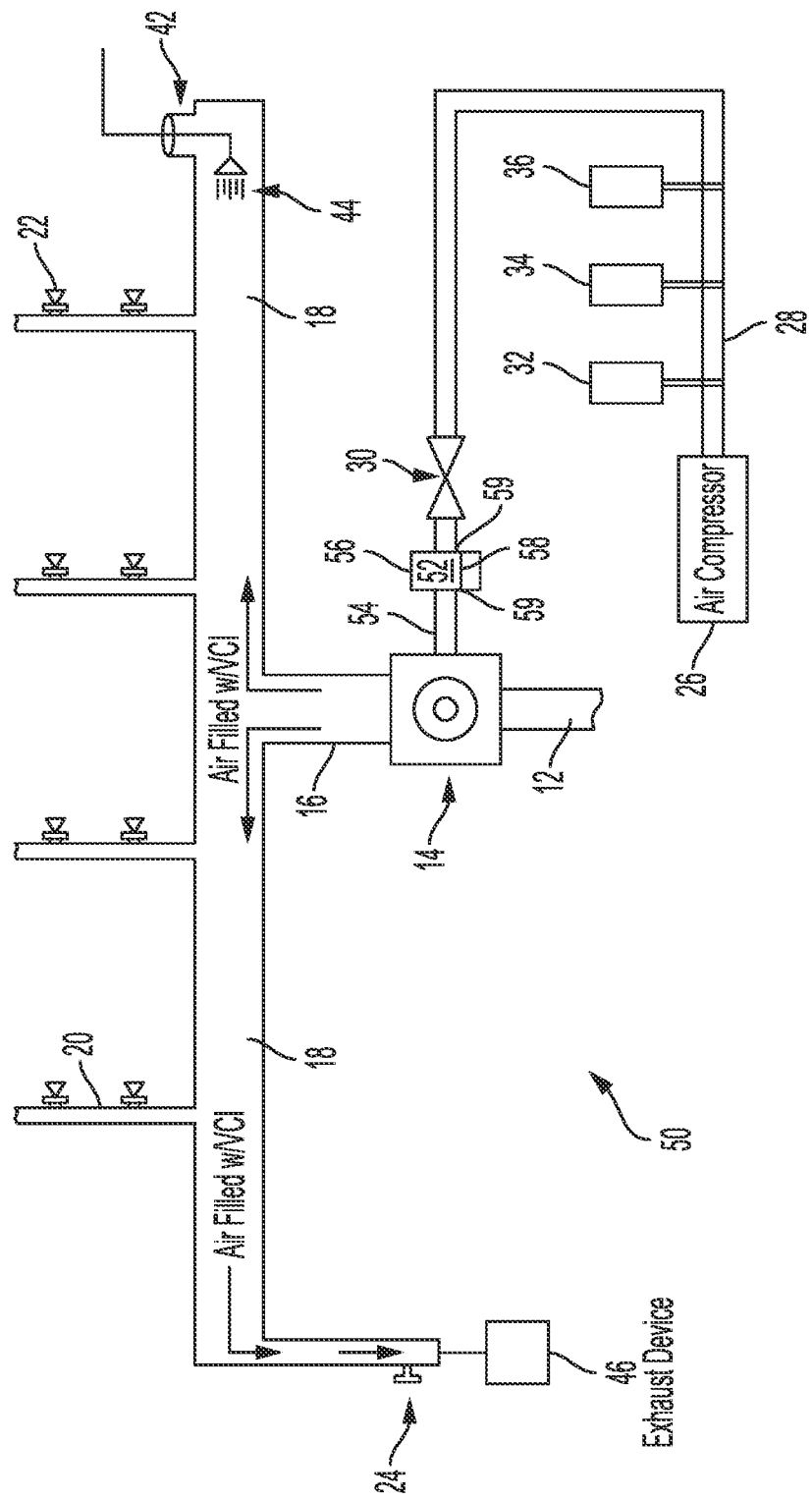
FIG. 3 is a schematic drawing of a second embodiment of a dry pipe sprinkler system in accordance with the present invention, including modifications to support introduction of a volatile corrosion inhibitor via the system used to fill the piping with pressurized gas.

FIG. 3 illustrates sprinkler system 50, which is a second embodiment of a dry pipe sprinkler system of the present invention. The sprinkler system 50 differs from sprinkler system 40 of FIG. 2 in that sprinkler system 50 includes housing unit 52 between air regulator 30 and check valve 14. Housing unit 52 is a chamber for holding VCI materials. In this embodiment, when air passes through housing unit 52, the air becomes enriched with VCI. The VCI-enriched air then flows through conduit 54 and check valve 14, and subsequently through connecting pipe 16, main pipe 18, and distribution pipes 20. The housing unit 52 preferably includes a vapor tight lid 56 that can be opened to add VCI materials to the housing unit, for example as powdered materials in porous pouches. Housing unit 52 optionally includes a porous barrier 58, such as a screen or perforated plate. Porous barrier 58 may, for example, hold pouches including VCI materials in one section of the housing unit 52. In this example, the vapor stream will become enriched in VCI as it passes through the housing unit 52. Porous barrier 58 may also be located between a portion of housing unit 52 containing a VCI agent in solid or liquid form, and a portion of housing unit 52 which is connected to conduit 54. VCI vapor generated from the sublimation or evaporation of the VCI agent may then pass through the porous barrier 58 and travel through conduit 54.

FIG. 3 shows housing unit 52 located between air regulator 30 and check valve 14. The housing unit 52 is located between two sections of conduit 54, with the conduit meeting the housing unit at two different positions 59 on the housing unit. However, in other embodiments, the housing unit 52 may be provided at different locations in sprinkler system 50. For example, housing unit 52 may be attached to air pipe 28 between air compressor 26 and air regulator 30, such that the housing unit 52 is located between two sections of air pipe 28, with the air pipe meeting the housing unit at two different positions on the housing unit.

The housing unit 52 may be removable or detachable from the remainder of sprinkler system 50, such that it may be separated from conduit 54. If the housing unit 52 is removable, the VCI in the housing unit may be replenished when the housing unit is separated from the remainder of the sprinkler system 50. Alternatively, the housing unit 52 may be included as a permanent, non-detachable portion of sprinkler system 50. For example, housing unit 52 may be bonded to conduit 54, such as by welding the housing unit to the conduit, or the housing unit 52 and conduit 54 may be formed from the same piece of metal to form a one-piece component of the system 50.

Sprinkler system 50 facilitates the long-term preservation of the pipes 16, 18, and 20 by allowing a continuous supply of VCI-rich air to be provided to the system via air compressor 26 and housing unit 52. It is possible to fill pipes 16, 18, and 20 by fogging VCI through inlet 44, as described above in connection with FIG. 2. Then the VCI-enriched air may be maintained by providing a continuous supply of VCI-rich air to the system 50 via air compressor 26 and housing unit 52, as described above in connection with FIG. 3. Alternatively, instead of fogging VCI through inlet 44, VCI may be initially provided to system 50 from the VCI released from housing unit 52.

With regard to the sprinkler systems 40, 50 of FIGS. 2-3, instead of fogging VCI through inlet 44, VCI may be sprayed through inlet 44 as a liquid. Accordingly, inlet 44 may take the form of a fogger or a liquid sprayer. Inlet 44 may remain within the sprinkler systems 40, 50. Alternatively, the inlet 44 may be removed after the initial distribution of VCI into the system through fogging or spraying.

FIG. 4 illustrates sprinkler system 60, which is a third embodiment of a dry pipe sprinkler system of the present invention. The sprinkler system 60 differs from sprinkler system 50 of FIG. 3 in that sprinkler system 60 does not include inlet 44. Sprinkler system 60 also does not include exhaust device 46, although an exhaust device may be included in other embodiments. Instead of fogging or spraying VCI from inlet 44, the VCI is initially provided to system 60 from the VCI released from housing unit 52. VCI-rich air is therefore provided to system 60 via air compressor 26 and housing unit 52.

FIG. 4 shows housing unit 52 located between air regulator 30 and check valve 14. The housing unit 52 is located between two sections of conduit 54, with the conduit meeting the housing unit at two different positions on the housing unit. However, in other embodiments, the housing unit 52 may be provided at different locations in sprinkler system 60. For example, housing unit 52 may be attached to air pipe 28 between air compressor 26 and air regulator 30, such that the housing unit 52 is located between two sections of air pipe 28, with the air pipe meeting the housing unit at two different positions on the housing unit.

The housing unit 52 may be removable or detachable from the remainder of sprinkler system 60, such that it may be separated from conduit 54. If the housing unit 52 is removable, the VCI in the housing unit may be replenished when the housing unit is separated from the remainder of the sprinkler system 60. Alternatively, the housing unit 52 may be included as a permanent, non-detachable portion of sprinkler system 60. For example, housing unit 52 may be bonded to conduit 54, such as by welding the housing unit to the conduit, or the housing unit 52 and conduit 54 may be formed from the same piece of metal to form a one-piece component of the system 60.

FIGS. 5-7 illustrate sprinkler system 70, which is a fourth embodiment of a dry pipe sprinkler system in accordance with the present invention. The sprinkler system 70 differs from the sprinkler system 60 of FIG. 4 in that sprinkler system 70 includes two exhaust devices: a first exhaust device 62 near the system drain 24, and a second exhaust device 64 near the opening 42.

FIGS. 5-7 show housing unit 52 located between air regulator 30 and check valve 14. The housing unit 52 is located between two sections of conduit 54, with the conduit meeting the housing unit at two different positions on the housing unit. However, in other embodiments, the housing unit 52 may be provided at different locations in sprinkler system 70. For example, housing unit 52 may be attached to air pipe 28 between air compressor 26 and air regulator 30, such that the housing unit 52 is located between two sections of air pipe 28, with the air pipe meeting the housing unit at two different positions on the housing unit.

The housing unit 52 may be removable or detachable from the remainder of sprinkler system 70, such that it may be separated from conduit 54. If the housing unit 52 is removable, the VCI in the housing unit may be replenished when the housing unit is separated from the remainder of the sprinkler system 70. Alternatively, the housing unit 52 may be included as a permanent, non-detachable portion of sprinkler system 70. For example, housing unit 52 may be bonded to conduit 54, such as by welding the housing unit to the conduit, or the housing unit 52 and conduit 54 may be formed from the same piece of metal to form a one-piece component of the system 70.

Figure 5:
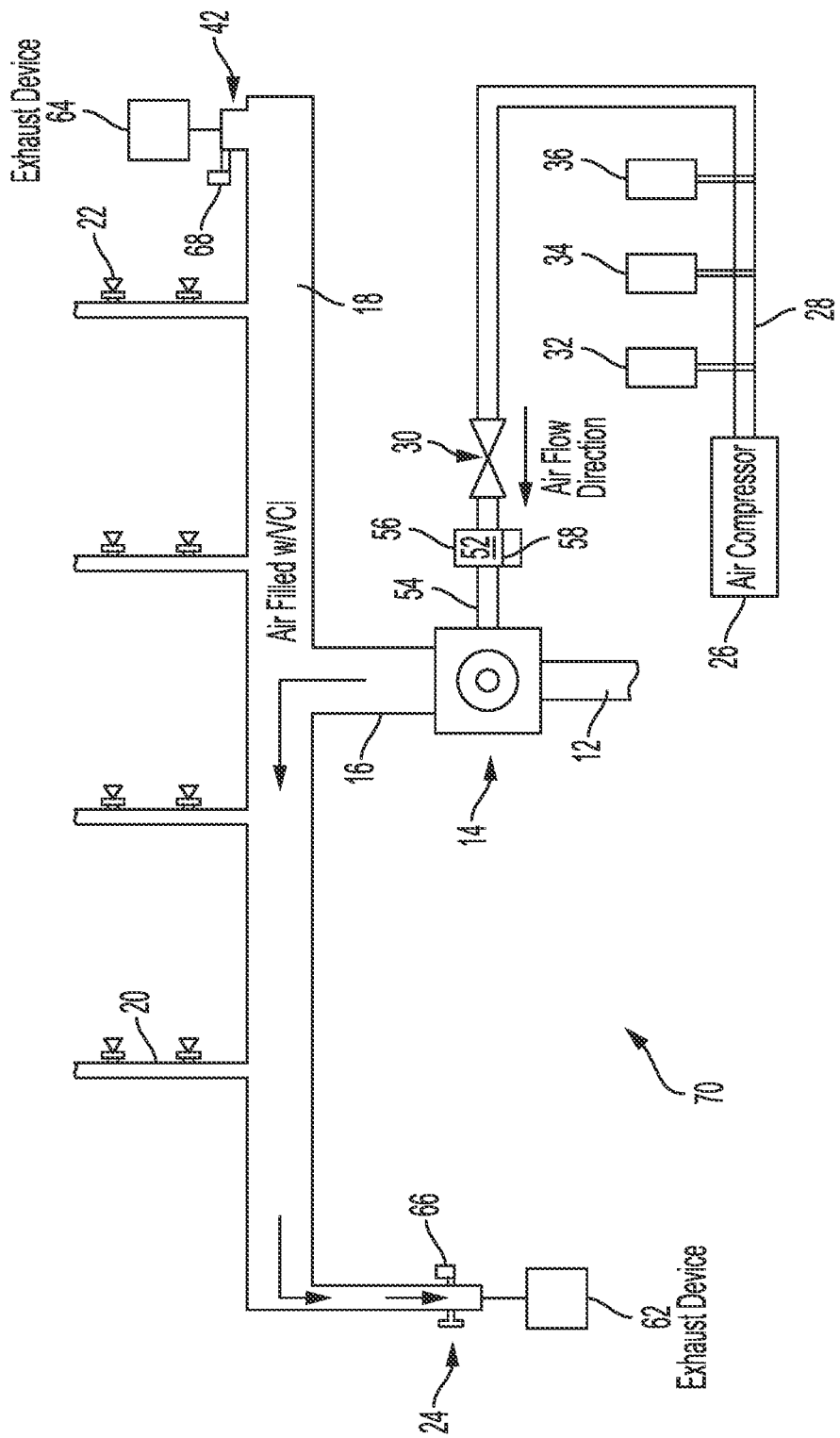
FIGS. 5-7 are schematic drawings of a fourth embodiment of a dry pipe sprinkler system in accordance with the present invention, including modifications to support introduction of a volatile corrosion inhibitor via the system used to fill the piping with pressurized gas.
Figure 6:
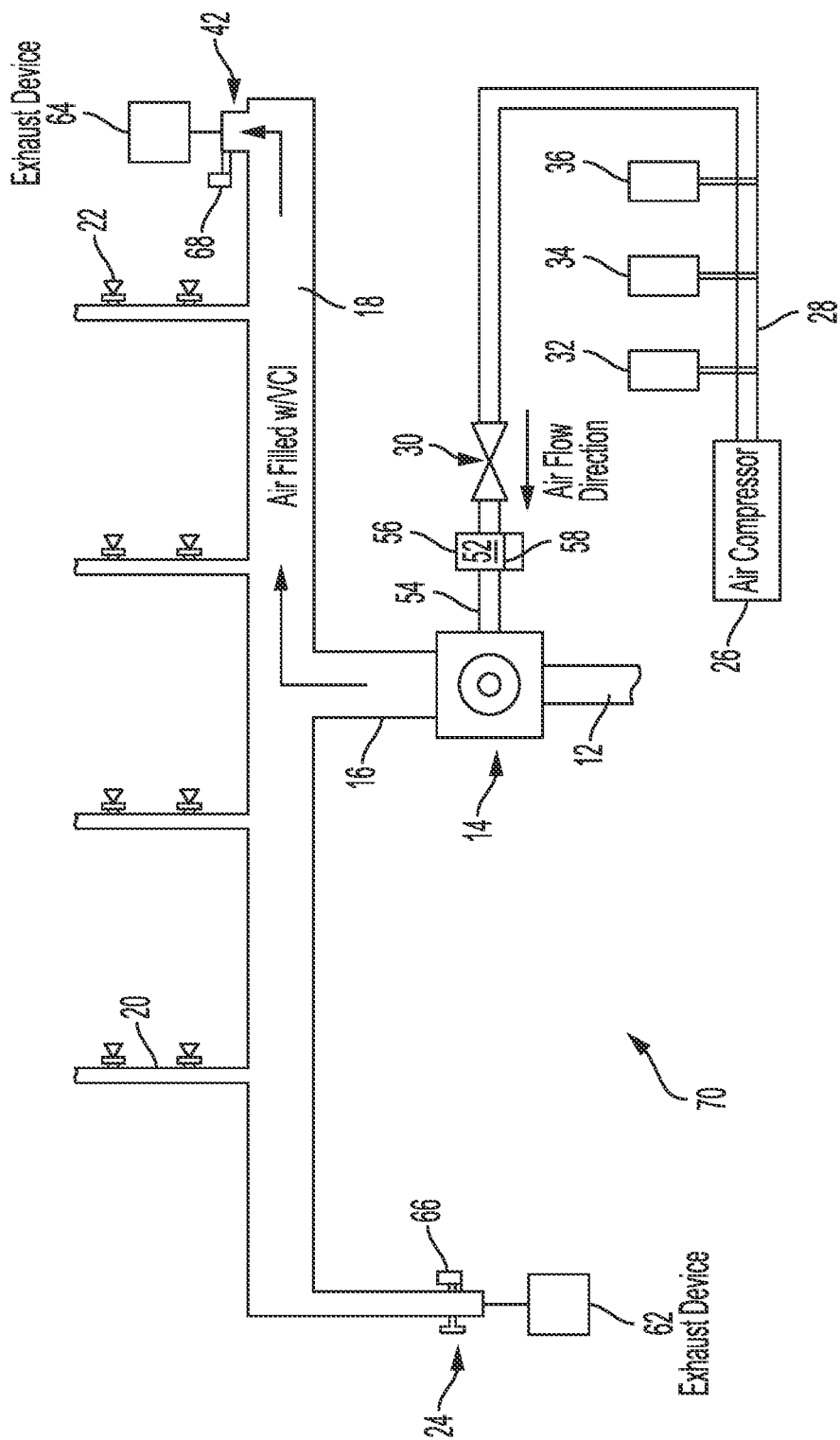
Figure 7:
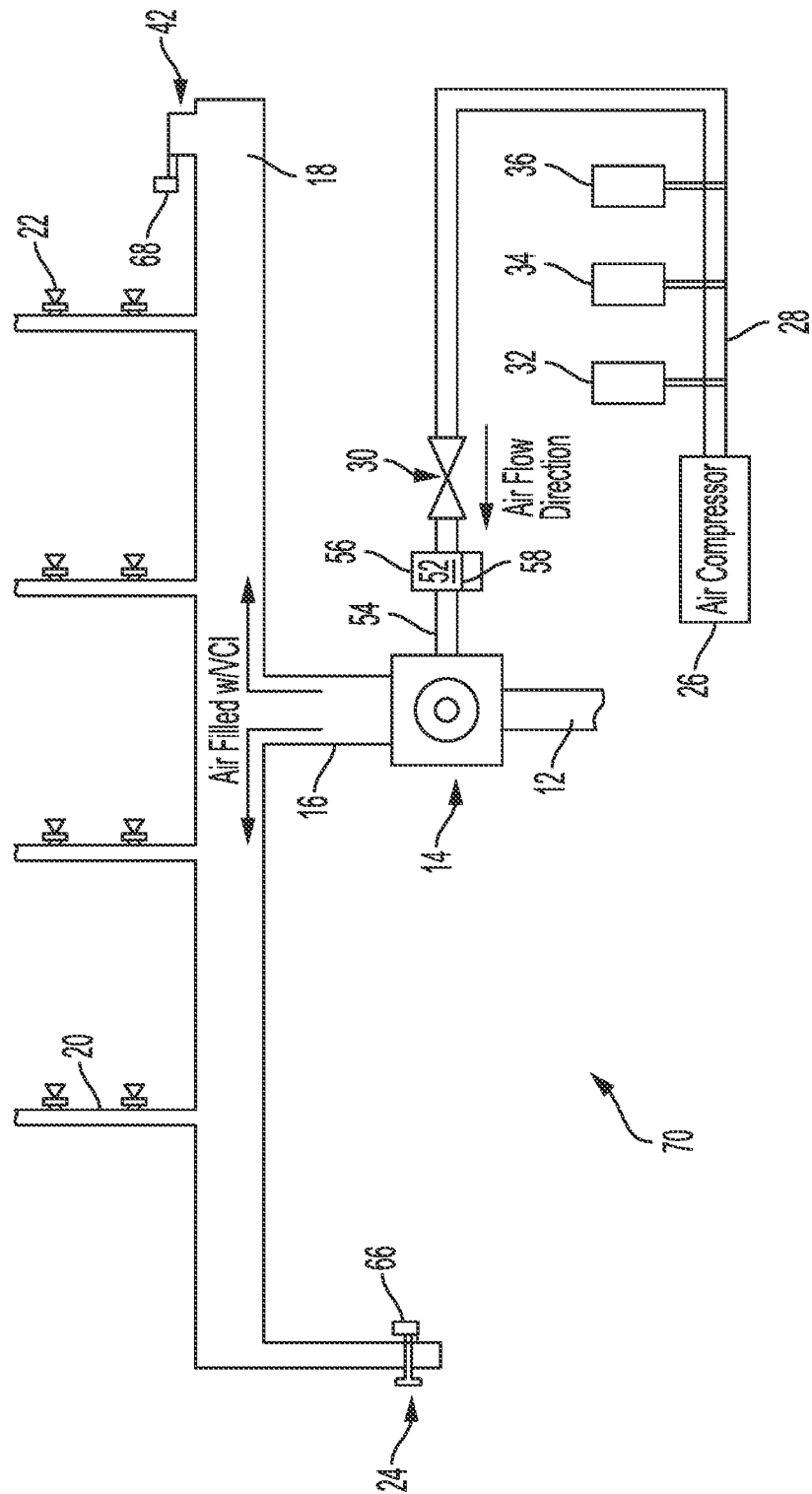

FIGS. 5-7 illustrate three steps that may be used to sequentially apply volatile corrosion inhibitor (VCI) to different portions of the piping system. FIG. 5 illustrates the first step of filling a first portion of the system with VCI. In this first step, opening 42 is closed, and system drain 24 is open. Air carrying VCI is pushed from air compressor 26 to system drain 24 with the aid of first exhaust device 62, which may be a vacuum pump or fan. A monitoring device 66 located near system drain 24 may be used to confirm the presence of VCI at the system drain at the end of the first step. For example, monitoring device 66 may be a VCI detector. In this first step, the use of first exhaust device 62 is optional.

FIG. 6 illustrates the second step of filling a second portion of the system with VCI. In this second step, opening 42 is open, and system drain 24 is closed. Air carrying VCI is pushed from air compressor 26 to opening 42 with the aid of second exhaust device 64, which may be a vacuum pump or fan. A monitoring device 68 located near opening 42 may be used to confirm the presence of VCI at the opening at the end of the second step. For example, monitoring device 68 may be a VCI detector. In this second step, the use of second exhaust device 64 is optional.

Although FIG. 6 shows monitoring devices 66, 68 located proximate to system drain 24 and opening 42 of the system 70, in other embodiments, monitoring devices may be in other locations in the system. For example, one or more monitoring devices may be located in distribution pipes 20, instead of or in addition to monitoring devices 66, 68. One or more monitoring devices may also be located along conduit 54 and/or pipes 16, 18, between housing unit 52 and opening 42, and/or between housing unit 52 and system drain 24. Monitoring devices may also be located proximate to the sprinkler heads 22 to detect VCI exiting the sprinkler heads. These monitoring devices may also be placed in the system instead of, or in addition to, monitoring devices 66, 68.

FIG. 7 illustrates the third step of preserving VCI in the sprinkler system 70 after it has been filled with VCI. In this third step, both opening 42 and system drain 24 are closed. Air carrying VCI is maintained in system 70 by pushing air from air compressor 26, passing the air through housing unit 52 so the air becomes enriched with VCI, and allowing the VCI-enriched air to flow through check valve 14 into connecting pipe 16, main pipe 18, and distribution pipes 20. Exhaust devices 62, 64 are not needed in this third step, when VCI is preserved in sprinkler system 70 after it has been filled with VCI. Therefore, exhaust devices 62, 64 may be removed from system 70 prior to this third step, and exhaust devices 62, 64 are not shown in FIG. 7.

In accordance with present invention, the preferred medium for delivering corrosion inhibiting agents to interior volume is an aerosol or vapor stream: more particularly, a non-reactive carrier gas with volatile corrosion inhibiting (VCI) agents in the carrier gas.

Many corrosion inhibiting chemicals useful for volatizing or sublimating can be prepared by reacting amines with acids. A useful mixture of inhibitors can be formed from cyclohexylammonium benzoate, monoethanolamine benzoate, and amorphous silica or other anti-caking agents. Monoethanolamine benzoate functions well, as does dicyclohexyl ammonium nitrate. Further well-functioning inhibitors include benzotriazole and the monoethanolamine salt of benzo- or tolyltriazole. Sodium nitrate also can be used. Different VCI agents typically have different equilibrium vapor pressures and different rates of volatilization at a given set of conditions. Thus, a blend of VCI agents may be advantageous in providing fast initial distribution of VCI agent in the interior volume as well as assuring longer term protection.

For example, Dicyclohexcyl Ammonium Nitrate, with a vapor pressure of $1.3\times10^{-4}$ (mm Hg) is an especially useful VCI for fast protection from corrosion. Cyclohexylammonium Benzoate, with a lower vapor pressure of $8\times10^{-5}$ (mm Hg), is useful for providing longer term protection.

Various means can be used to verify that sufficient VCI agent has been distributed in the interior volume. Vapor samples can be collected and analyzed by GC (Gas Chromatography), MS (Mass Spectrometry), or IR (Infrared spectroscopy) to estimate concentration of the VCI present. Other instruments designed for detection of low levels of volatile organic compounds may be used. Alternately, colorimetric test strips produced by the Cortec Corporation can be placed in the interior space near an exit port. These will change color when the vapor space contains sufficient VCI agent to provide corrosion protection. Other suitable analytical methods may be applied.

Some examples of suitable corrosion inhibiting formulas are as follows:

| Component | Percent by Weight |
|---|---|
| Formulation 1 | |
| Cyclohexylammonium Benzoate | 84-90 |
| Monoethanolamine Benzoate | 7-12 |
| Amorphous Silica | 3-4 |
| Formulation 2 | |
| Cyclohexylammonium Benzoate | 60 |
| Monoethanolamine Benzoate | 20 |
| Dicyclohexcyl Ammonium Nitrate | 20 |
| Formulation 3 | |
| Cyclohexylammonium Benzoate | 55 |
| Monethanolamine Benzoate | 20 |
| Dicyclohexcyl Ammonium Nitrate | 20 |
| Benzotriazole | 5 |
| Formulation 4 | |
| Cyclohexylammonium Benzoate | 3-5% |
| Ammonium Benzoate | 12-15% |
| Sorbitan Monolaurate, ethoxylated | 2-3% |
| Water | 77-84% |
| Formulation 5 | |
| Cyclohexylammonium Benzoate | 5-10% |
| Monoethanol Ammonium Benzoate | 15-20% |
| Salt of Tall Oil Hydroxyethyl Imidazoline | 1-5% |
| Water | 65-70% |
| Formulation 6 | |
| Ammonium Benzoate | 80-90% |
| Sodium Alkylnaphthalene Sulfonate | 5-10% |
| Triethanolammonium Nitrate | 1-5% |
| Formulation 7 | |
| Monoethanol Ammonium Benzoate | 15-20% |
| Triethanolammonium Salt of Isonanoic Acid | 25-35% |
| Water | 45-60% |
| Formulation 8 | |
| Cyclohexanamine benzoate | 60-70% |
| Ethanol ammonium benzoate | 5-10% |

-continued

| Component | Percent by Weight |
|---|---|
| Benzotriazole | 5-10% |
| Triethanolamine nitrate | 15-25% |
| Formulation 9 | |
| Triethanolamine nitrate | 6%-12% |
| Tolytriazole | 9%-12% |
| Cyclohexanamine benzoate | 15%-21% |
| Ethanol ammonium benzoate | 39%-45% |
| Tall oil imidazoline acetate | 6%-9% |
| Tall oil imidazoline nitrate | 3%-9%. |
| Formulation 10 | |
| Cyclohexanamine benzoate | 19%-38% |
| Ethanol ammonium benzoate | 46%-69% |
| Tall oil imidazoline acetate | 11%-19% |
| 2-aminoethanol | 4%-11%. |
| Formulation 11 | |
| Cyclohexanamine benzoate | 4-8% |
| Ethanol ammonium benzoate | 48-56% |
| Benzotriazole | 4-8% |
| Triethanolamine nitrate | 12-20% |
| Ethanol | 16-24% |
| Formulation 12 | |
| Benzotriazole | 5-10% |
| Sodium sebacate | 55-65% |
| Ammonium benzoate | 15-25% |
| Silica | 0-5% |
| Dicyclohexylamine Nitrite | 5-10% |
| Sodium molybdate | 5-10% |
| Formulation 13 | |
| Dicyclohexylamine Nitrite | 5-25% |
| Benzotriazole | 5-25% |
| Cyclohexanamine benzoate | 20-50% |
| Monoethanolamine benzoate | 20-50% |
| Formulation 14 | |
| Dicyclohexylamine Nitrite | 20-60% |
| Cyclohexanamine benzoate | 40-80% |
| Formulation 15 | |
| Cyclohexanamine benzoate | 50-95% |
| Monoethanolamine Benzoate | 5-50% |
| Formulation 16 | |
| Cyclohexanamine M-MononitroBenzoate | 30-60% |
| Diethanolamine Benzoate | 10-90% |
| Tolyltriazole | 10-40% |
| Formulation 17 | |
| Benzotriazole | 5-40% |
| Cyclohexanamine Benzoate | 25-50% |
| Monoethanolamine Benzoate | 25-50% |
| Formulation 18 | |
| Benzotriazole | 2-5% |
| Cyclohexanamine Benzoate | 25-50% |
| Monoethanolamine Benzoate | 25-50% |
| Tall Oil Imidazoline nitrate | 3-20% |

EXAMPLES

Example 1

For a dry pipe sprinkler system 40, such as seen schematically in FIG. 2, an aerosol of a liquid corrosion inhibitor composition, such as Formulation 10 dissolved in water (30% by weight) is introduced into the interior piping 16, 18, and 20 through inlet 44 aided by a liquid sprayer. The process is continued until liquid aerosol is observed in the gas leaving system drain 24.

Example 2

For a dry pipe sprinkler system 40, such as seen schematically in FIG. 2, an aerosol of a powdered solid inhibitor composition, such as Formulation 1 is introduced into the interior piping 16, 18, and 20 through inlet 44 aided by a fan or blower. The process is continued until powder is observed in the gas leaving system drain 24.

Example 3

For a dry pipe sprinkler system 50, such as seen schematically in FIG. 3, an aerosol of a powdered solid inhibitor composition, such as Formulation 1 is introduced into the interior piping 16, 18, and 20 through inlet 44 aided by a fan or blower. The process is continued until powder is observed in the gas leaving the exit port near system drain 24. A porous pouch containing a powder corrosion inhibitor composition, such as Formulation 1, is located in the housing unit 52. After pipes 16, 18, and 20 have initially been filled with VCI-rich air as described above, VCI-rich air is maintained in the system by passing pressurized air from the air compressor 26 through the housing unit 52 and into the pipes 16, 18, and 20 at a slow flow. The process is continued until VCI is detected at all exit ports, including at system drain 24, opening 42, and sprinkler heads 22.

Example 4

Figure 4:
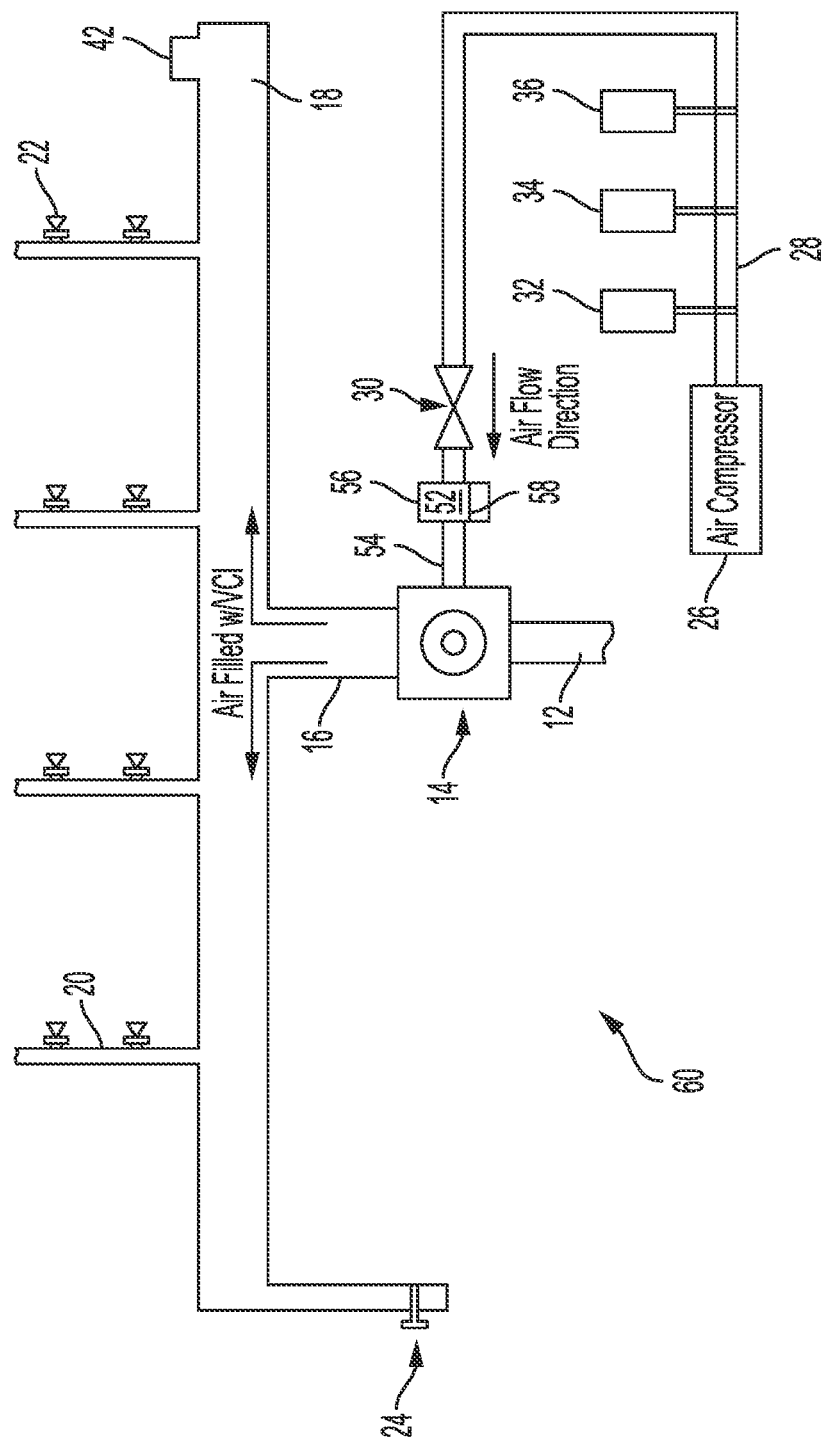
FIG. 4 is a schematic drawing of a third embodiment of a dry pipe sprinkler system.

For a dry pipe sprinkler system 60, such as seen schematically in FIG. 4, a porous pouch containing a powder corrosion inhibitor composition, such as Formulation 12, is located in the housing unit 52. Pressurized air from the air compressor 26 is passed through the housing unit 52 and into the pipes 16, 18, and 20 at a slow flow. The process is continued until VCI is detected at all exit ports, including at system drain 24, opening 42, and sprinkler heads 22.

Example 5

For a dry pipe sprinkler system 70, such as seen schematically in FIGS. 5-7, a porous pouch containing a powder corrosion inhibitor composition, such as Formulation 12, is located in the housing unit 52. In a first step, as shown in FIG. 5, opening 42 is closed, and system drain 24 is open. Pressurized air from the air compressor 26 is passed through the housing unit 52 and into the pipes 16 and 18 toward system drain 24, with the aid of first exhaust device 62. This first step is continued until VCI is detected by monitoring device 66. Then the system drain 24 is closed, and opening 42 is opened, for the second step of filling system 70 with VCI-rich air. In the second step, as shown in FIG. 6, pressurized air from the air compressor 26 is passed through the housing unit 52 and into the pipes 16 and 18 toward opening 42, with the aid of second exhaust device 64. This second step is continued until VCI is detected by monitoring device 68. Then the opening 42 is closed for the third step of the process, as shown in FIG. 7. In the third step of the process, which is the maintenance of VCI in system 70, both opening 42 and system drain 24 are closed. To maintain VCI-rich air in the system 70, pressurized air from the air compressor 26 is passed through the housing unit 52 and into pipes 16, 18, and 20. The presence of VCI at system drain 24 and opening 42 may be detected by monitoring devices 66 and 68. Additional monitoring devices may also be used to detect VCI at sprinkler heads 22.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A corrosion protection system, comprising:
   a conduit having an interior surface configured for carrying a fluid capable of corroding the interior surface over time;
   a first port through which fluid is capable of entering the conduit;
   a second port through which fluid is capable of exiting the conduit;
   a first source configured for the introduction of a volatile corrosion inhibitor into the conduit such that the volatile corrosion inhibitor is able to travel from the first source of the volatile corrosion inhibitor to the interior surface of the conduit;
   a second source configured for the introduction of the volatile corrosion inhibitor into the conduit, independent from the first source, such that the volatile corrosion inhibitor is able to travel from the second source of the volatile corrosion inhibitor to the interior surface of the conduit; and
   a monitoring device configured for detecting the presence of the volatile corrosion inhibitor in the conduit, where the volatile corrosion inhibitor is from either the first or second source.

2. The system of claim 1, wherein the first source of the volatile corrosion inhibitor is a fogger, a sprayer, or a combination thereof, and second source of the volatile corrosion inhibitor is introduced from a housing unit.

3. The system of claim 1, wherein the volatile corrosion inhibitor is selected from the group of constituents consisting of: amine salts of nitrates, amine salts of nitrites, amine salts of organic acids, amine carboxylates, ammonium salts of organic acids, alkali dibasic acid salts, amine dibasic acid salts, alkali nitrites, alkali nitrates, alkali molybdates, tall oil imidazolines, volatile amines, volatile organic acids, triazole compounds, and their combinations.

4. The system of claim 1, wherein the volatile corrosion inhibitor is selected from the group consisting of: ammonium benzoate, cyclohexylammonium benzoate, monoethanolamine benzoate, dicyclohexyl ammonium nitrate, benzotriazole, tolyltriazole, amine carboxylates, amine salts of caprylic acid, amine salts of sebacic acid, and their combinations.

5. The system of claim 1, further comprising a device to facilitate transport of the volatile corrosion inhibitor from the first or second source to the interior surface of the conduit.

6. The system of claim 5, wherein the device to facilitate transport of the volatile corrosion inhibitor comprises a fan, a blower, a compressor, a pump, or a combination thereof.

7. The system of claim 1, wherein the second port comprises a plurality of sprinkler heads, and the conduit is a pipe of a dry pipe sprinkler system.

8. The system of claim 1, wherein the second port comprising a plurality of additional ports through which fluid is capable of exiting the conduit.

9. The system of claim 1 where at least one of the sources of introduction of the volatile corrosion inhibitor is a detachable housing.

10. The system of claim 1 further comprising a valve configured for selectively introducing the fluid into the conduit, and at least one of the sources for the introduction of the volatile corrosion inhibitor is through the valve, where the valve selects between introduction of the fluid and the inhibitor.

11. The system of claim 1 further comprising:
   a third port through which fluid is configured to exit the conduit;
   a first device at the second port to facilitate transport of the volatile corrosion inhibitor from the first source for the introduction of the volatile corrosion inhibitor to the second port;
   a second device at the third port to facilitate transport of the volatile corrosion inhibitor from the second source for the introduction of the volatile corrosion inhibitor to the third port; and
   wherein the first and second devices are selectively and independently engaged to direct the movement of the volatile corrosion inhibitor to one of, or both of, the second and third exit ports.

12. A corrosion protection system, comprising:
   a conduit having an interior surface capable of carrying a fluid capable of corroding the interior surface;
   a first exit port through which fluid is capable of exiting the conduit;
   a second exit port through which fluid is capable of exiting the conduit;
   a monitoring device capable of detecting the presence of a volatile corrosion inhibitor;
   a dispensing unit containing the volatile corrosion inhibitor, wherein the dispensing unit is in communication with the conduit such that the volatile corrosion inhibitor is able to travel from the dispensing unit of the volatile corrosion inhibitor to the interior surface of the conduit;
   a first device at the first exit port to facilitate transport of the volatile corrosion inhibitor from the dispensing unit to the first exit port;
   a second device at the second port to facilitate transport of the volatile corrosion inhibitor from the dispensing unit to the second exit port; and
   wherein the first and second devices are be selectively and independently engaged to direct the movement of the volatile corrosion inhibitor from the dispensing unit to one, or both, of the first and second exit ports.

13. The system of claim 12, wherein the volatile corrosion inhibitor is supplied to the dispensing unit in a solid form, in a liquid form, or as a composition impregnated in a substrate.

14. The system of claim 12, wherein the volatile corrosion inhibitor is selected from the group of constituents consisting of: amine salts of nitrates, amine salts of nitrites, amine salts of organic acids, amine carboxylates, ammonium salts of organic acids, alkali dibasic acid salts, amine dibasic acid salts, alkali nitrites, alkali nitrates, alkali molybdates, tall oil imidazolines, volatile amines, volatile organic acids, triazole compounds, and their combinations.

15. The system of claim 12, wherein the first and second devices to facilitate transport of the volatile corrosion inhibitor from the dispensing unit to the interior surface of the conduit, comprises a fan, a blower, a compressor, a pump, or a combination thereof.

16. The system of claim 12, further comprising an additional exit port, wherein the additional exit port comprises a sprinkler head, and the conduit is a pipe of a dry pipe sprinkler system.

17. The system of claim 12, further comprising a corrosion monitoring device located inside the conduit to monitor a rate of corrosion.

18. The system of claim 12, wherein the volatile corrosion inhibitor is in a solid form and is enclosed in a vapor permeable pouch.

19. The system of claim 12 where the dispensing unit is detachable.

20. A corrosion prevention process for protection of a conduit, comprising:
providing a volatile corrosion inhibitor in a housing unit connected to the conduit;
allowing the volatile corrosion inhibitor to be distributed into a volume of gas in the conduit;
moving said gas through an interior volume of the conduit from a first and second independent source, to apply said volatile corrosion inhibitor to interior portions of the conduit;
using a monitoring device to detect the volatile corrosion inhibitor at an exit port of the conduit.

21. The process of claim 20, wherein the volatile corrosion inhibitor is distributed into the volume of gas through evaporation or sublimation of the volatile corrosion inhibitor.

22. The process of claim 20, wherein the volatile corrosion inhibitor is supplied to the housing unit in a solid form, in a liquid form, or as a composition impregnated in a substrate.

23. The process of claim 20, wherein the volatile corrosion inhibitor is distributed into the volume of gas as an aerosol, and wherein said aerosol comprises liquid droplets, solid particles, or a combination thereof.

24. The process of claim 20, wherein a means for moving said gas comprises: a fan, a blower, a compressor, a pump, or a combination thereof.

25. The process of claim 20, further comprising using a corrosion monitoring device to monitor a rate of corrosion in the conduit.

26. The process of claim 20, wherein the volatile corrosion inhibitor is in a solid form and is enclosed in a vapor permeable pouch.

* * * * *